United States Patent [19]

Bortolaso et al.

[11] Patent Number: 5,663,360
[45] Date of Patent: Sep. 2, 1997

[54] **PROCESS FOR PREPARING [R-(R*,R*)]-5-(3-CHLOROPHENYL)-3-[2-(3,4-DIMETHOXYLPHENYL)-1-METHYL-ETHYL]-OXAZOLIDIN-2-ONE**

[75] Inventors: Roberto Bortolaso; Mariano Stivanello, both of Vicenza, Italy

[73] Assignee: F.I.S. Fabbrica Italiana Sintetici S.p.A., Vicenza, Italy

[21] Appl. No.: 632,076

[22] Filed: Apr. 15, 1996

[30] Foreign Application Priority Data

May 25, 1995 [IT] Italy ................................ MI95A1073

[51] Int. Cl.$^6$ ........................................... C07D 263/20
[52] U.S. Cl. .................................................. 548/229
[58] Field of Search ..................................... 548/229

[56] References Cited

U.S. PATENT DOCUMENTS 5,461,163  10/1995  Bellon ..................................... 548/229

*Primary Examiner*—Robert Gerstl
*Attorney, Agent, or Firm*—Diller, Ramik & Wight, PC

[57] ABSTRACT

The present invention relates to a process for preparing [R-(R*,R*)]-5-(3-chlorophenyl)-3-[2-(3,4-dimethoxyphenyl)-1-methyl-ethyl]-oxazolidin-2-one of Formula (1), characterized in that said process comprises the step of reacting (R)-3,4-methoxy-amphetamine of Formula (3), with (R)-3-chloro-mandelic acid, of Formula (9):

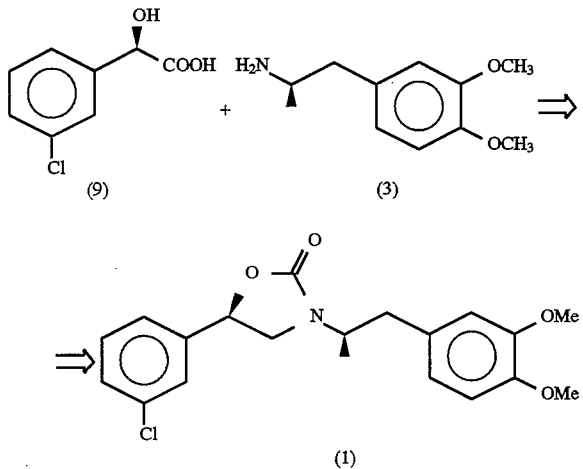

4 Claims, No Drawings

PROCESS FOR PREPARING [R-(R*,R*)]-5-(3-CHLOROPHENYL)-3-[2-(3,4-DIMETHOXYLPHENYL)-1-METHYL-ETHYL]-OXAZOLIDIN-2-ONE

The present invention relates to a novel process for preparing [R-(R*,R*)]-5-(3-chlorophenyl)-3-[2-(3,4-dimethoxyphenyl)-1-methyl-ethyl]-oxazolidin-2-one (1), having the Formula

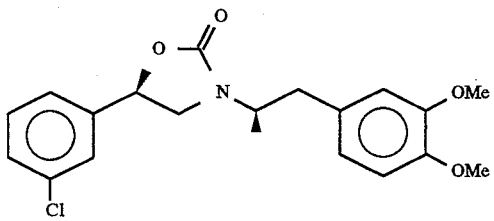

This compound is an advanced intermediate in the synthesis of [R-(R*,R*)]-5-{[(2-(3-chlorophenyl)-2-hydroxyethyl)-amino]-propyl}-1,3-benzodioxole-2,2-dicarboxy acid, disodium salt (2)

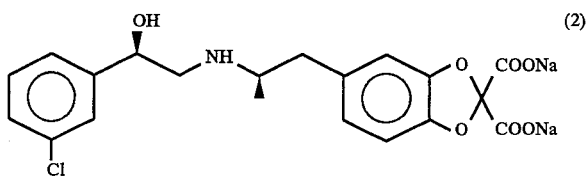

This benzodioxole-phenethanolamine (2), synthetised in Lederle Laboratories of American Cyanamid, is a powerful β-adrenergic agonist and displays a marked antidiabetic and antiobesity activity (J. D. Bloom, U.S. Pat. Nos. 5,061,727; 5,106,867; J. Med. Chem. 1992, 35, 3081–3084).

Such a molecule (2) exerts a considerable activity on β3 receptors responsible for lypolisis of adipocytes, but displays an extremely low effectiveness on β1 and β2 receptors, respectively responsible for stimulation of atrial rate and of glycogen cleavage in muscle; this high selectivity on β3 receptors of this agent reduces the undesired side effects (tachycardia and muscular tremors), down to a negligible level—which, on the contrary, are present in other, similar, phenethanolaminic derivatives.

The phenethanolaminic derivative (2) has two chiral centers and the lypolytic activity is only shown by the (R,R)-enantiomer.

Therefore, it is necessary that a method of chiral synthesis is developed, with a stereo chemical control of each individual reaction.

J. D. Bloom et al., in the references cited above, introduce a synthesis for racemic benzodioxole-phenethanolamine (2), outside of the scope of the present patent, and a chiral synthesis, using (R)-3,4-dimethoxy-amphetamine (3)

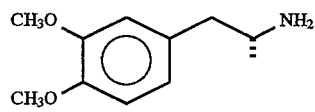

and (R)-3-chloro-styrene oxide (4)

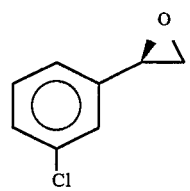

as starting materials.

The coupling reaction of these chiral raw materials leads to the formation of (R,R)-1-(3-chlorophenyl)-2-[2-(3,4-dimethoxyphenyl)-1-methyl-ethyl-amino]-ethanol (5), with the initial chirality being completely retained.

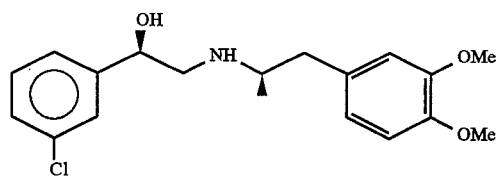

From the reaction of (R,R)-phenethanolamine (5) with carbonyldiimidazole, (R,R)-5-(3-chlorophenyl)-3-[2-(3,4-dimethoxyphenyl)-1-methylethyl]-oxazolidine-2-one (1) is obtained in a yield of 60% [based on amphetamine (3)], and 98% pure.

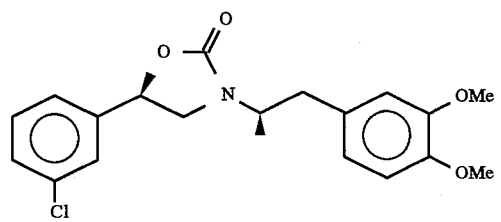

(R,R)-oxazolidinone (1) is finally converted into (R,R)-benzodioxole-phenethanolamine (2) through three additional steps, which comprise:

1. Demethylation of both methoxy groups with boron tribromide;
2. Reaction of dihydroxy-derivative (6) with dibromo-diethyl-malonate;
3. Basic hydrolysis of diester (7) with the end product (2) being obtained.

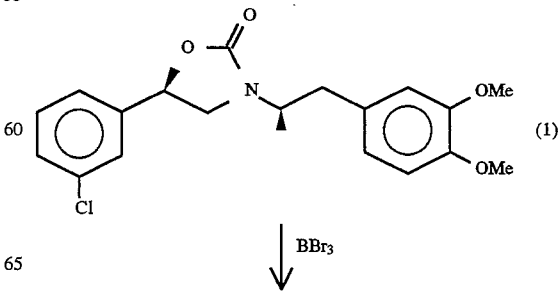

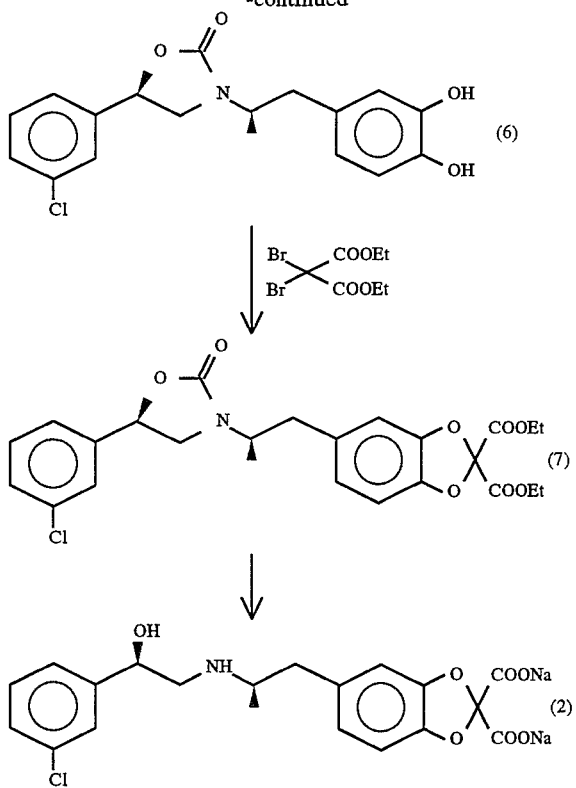

Also the latter steps take place with chirality being completely retained.

J. D. Bloom et al. have also developed the synthesis of both chiral starting materials (3) and (4), key intermediates for the whole process for benzo-dioxolenethanolamine (2) synthesis.

The synthesis of (R)-3,4-dimethoxyamphetamine (2) is carried out (according to U.S. Pat. No. 5,061,727) through 6 steps by starting from L-DOPA (8),

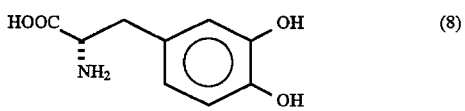

in an overall yield of 32% and using an expensive raw material (L-DOPA) and some expensive reactants (di-tert.-butyl dicarbonate and lithium borohydride) and/or toxic reactants (methyl iodide, trifluoro-acetic acid).

In J. Med. Chem 1992, 35, 3081–3084 (R)-3-clorostyrene oxide (4) is synthetised through 3 steps from 3-chloroacetophenone, in overall yield of 32%; key reaction is an enantioselective reduction of carbonyl group into a chiral secondary alcohol, in which a chiral oxazaborolidine is used—(a complex of diborane with a derivative of D-proline), a reactant not to be found on the market and with a surely very high cost (in fact, it is derived from a non-natural, expensive aminoacid, see E. J. Corey et al., "J. Am. Chem. Soc." 1987, 109, 5551–5553, 7925–7926).

In pertinent technical literature, further methods are reported for the synthesis of both (R)-3,4-dimethoxyamphetamine (3) and of (R)-3-chlorostyrene oxide (4): unfortunately, all of them suffer from the drawback of requiring expensive chiral reactants and/or enzymatic technologies which, in their turn, require special equipment. Some of these display also considerable problems in case of industrial application.

Both above products are also available from the market at a price which is presently very high.

The subject-matter of the present invention is an alternative synthesis for the derivatives of oxazolidinone (1) as defined above, which synthesis, as compared to the known synthesis developed at Lederle Laboratories and remainded above, achieves the following main purposes:

the product is synthetised according to a more direct route, in higher overall yields and with an extremely good purity level;

expensive raw materials which are difficult to find and/or particularly toxic, are avoided;

no particular, sophisticated technologies are used;

the whole synthesis displays a considerably high productivity and is easily scaled up with good scale economies.

Summing-up, achieving such purposes would allow the industrial costs of the product in question to be considerably reduced.

Such purposes are achieved according to the present invention by means of a process for preparing [R-(R*,R*)]-5-(3-chlorophenyl)-3-[2-(3,4-dimethoxyphenyl)-1-methylethyl]-oxazolidin-2-one, of Formula (1), characterized in that said process comprises the step of reacting (R)-3,4-dimethoxyamphetamine of Formula (3), with (R)-3-chloromandelic acid of Formula (9),

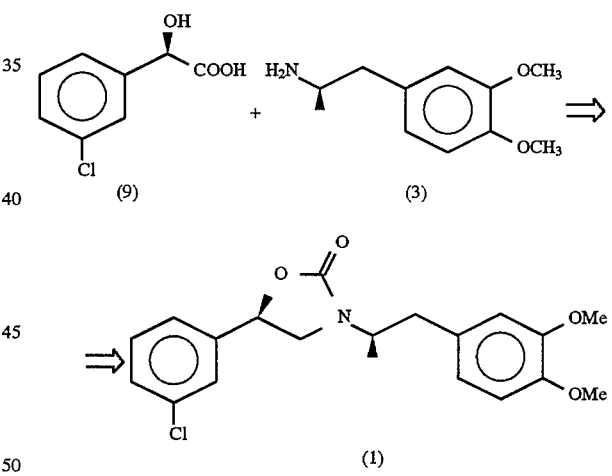

The present invention is disclosed now in greater detail, as follows. Let us take into consideration the end synthesis reaction between (R)-3,4-dimethoxyamphetamine (3) and (R)-3-chloromandelic acid (9), schematically shown as follows:

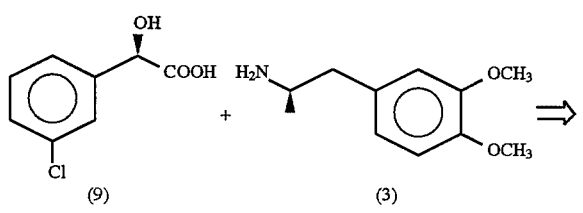

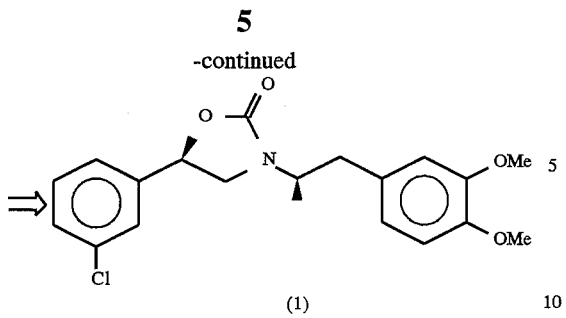

(1)

selectively reduced to the intermediate product, (R,R)-N-phenylethyl-3,4-dimethoxy-amphetamine (15) hydrochloride by catalytic hydrogenation with Raney-Nickel. The intermediate (15) is finally debenzylated by hydrogenation, to form (R)-3,4-dimethoxyamphetamine (3) hydrochloride.

As previously mentioned, (R)-3,4-dimethoxyamphetamine (3) is known and available from the market at a very high price (it is produced by starting from racemic amphetamine by an enzymatic route), whereas (R)-3-chloromandelic acid is not yet available; on the contrary, the racemic acid is an available product on the market (even if not on a large scale), also with a rather high price.

Starting from these presuppositions, an asimmetric synthesis of (R)-3,4-dimethoxy-amphetamine (3) and an original method for resolving (R)-3-chloromandelic acid (9) from the corresponding racemate were developed.

Synthesis of (R)-3,4-dimethoxy-amphetamine

SCHEME I

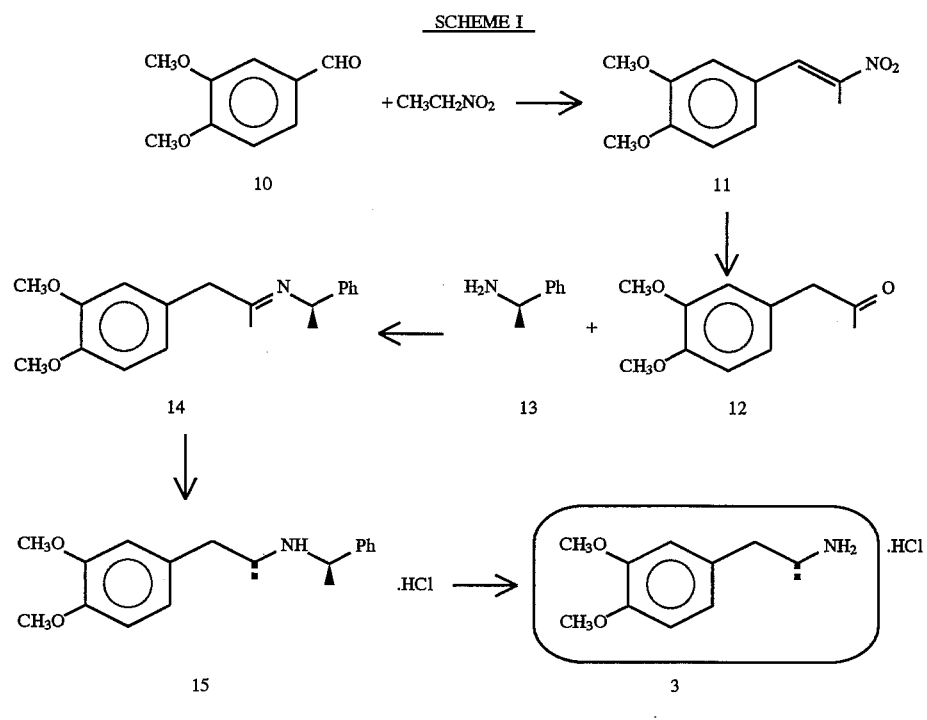

According to the present invention, (R)-3,4-dimethoxyamphetamine (3) is prepared according to the synthesis depicted in following Scheme I whereby the starting material 3,4-dimethoxy-benzaldehyde (veratric aidehyde) (10), which is a cheap raw material available from the market, is condensed with nitroethane (Henry's reaction), to form 3,4-dimethoxy-phenyl-2-nitropropene (11), which is then suitably reduced to an intermediate, i.e., 3,4-dimethoxy-phenyl-acetone (12) by means of a catalytic hydrogenation. The intermediate (12) is then reacted with an optically active amine, (R)-α-methyl-benzyl-amine (13) to form the corresponding chiral imine (14). In a key step of the present synthesis, the chiral amine (14) is diastereo-selectively reduced to the intermediate product, (R,R)-N-phenylethyl-3,4-dimethoxy-amphetamine (15) hydrochloride by catalytic hydrogenation with Raney-Nickel. The intermediate (15) is finally debenzylated by hydrogenation, to form (R)-3,4-dimethoxyamphetamine (3) hydrochloride.

Summing-up, the amphetamine (3) is syntehtised in 5 steps which, however, imply that only two intermediates are isolated and purified: 3,4-dimethoxyphenyl-2-nitropropene (11) and (R,R)-N-phenyl-ethyl-3,4-dimethoxyamphetamine (15). The overall yield of the process is of 60–62% and the purity of amphetamine, both chemical and optical, is of higher than 99%.

The first step of this synthesis, i.e., the condensation of veratric aldehyde (10) with nitro-ethane in the presence of ammonium acetate is a known synthesis from literature (see, for example, D. E. Nichols et al., "J. Med. Chem." 1991, 34, 1662–1668): owing to the rather high cost of nitro-ethane, some parameters of the synthesis were optimized (e.g.:

nitro-ethane amount, temperature, reaction time, purification method), with intermediate (11) being obtained in good yields (85–87%) and with a high purity level (>99.5%).

The second step is the partial reduction of nitro-propene (11) into 3,4-dimethoxy-phenyl-acetone (12): in literature, a large number of methods are reported for such a reduction (see, e.g., the reviews by A. G. M. Barrett in "Chem. Rev." 1986, 86, 751–762 and by G. W. Kabalka et al. In "Tetr.", 1990, 46, N. 21, 7443–7457); many of them require the use of particular, expensive and/or toxic reducing agents (lithium trialkyl borohydrides, chromium-(II) chloride, tributyl-tin hydride/m-chloro-perbenzoic acid, sodium stannite, zinc borohydride, lead in acetic acid, Raney nickel in sodium hypophosphite); or, supply only low yields (reaction with iron in hydrochloric acid). From literature, also some methods of catalytic hydrogenation are known: with palladium on carbon in pyridine or in methanol/hydrochloric acid (see W. K. Seifert and P. C. Condit, "J. Org. Chem.", 1963, 28, 265–267 and S. Mutak et al. "Kem. Ind.", 1986, 10, 523–5256). In both cases, a mixture is obtained of phenyl-acetone and its corresponding oxime, which is converted into phenyl-acetone by means of a trans-oximation reaction with aqueous formaldehyde.

The method by Mutak et al. proved to be excellent in our synthesis: the hydrogenation is carried out at room temperature in alcoholic solvent containing diluted aqueous sulfuric acid; as catalyst, Pd/C is used, which is also recyclable several times. The use of sulfuric acid instead of hydrochloric acid yields a "cleaner" reaction: at the end of hydrogen consumption, a mixture is obtained of phenyl-acetone (12) and of its corresponding oxime: by reaction with aqueous formaldehyde in two-phase organic solvent/aqueous sulfuric acid mixture, 3,4-dimethoxy-phenyl-acetone (12) is obtained in quantitative yield with a purity of >98%, i.e., pure enough to be used in the subsequent step without any further purifications.

Other methods for hydrolising the oxime into phenyl-acetone did not yield analogous results to those obtained with formaldehyde: owing to the matter of fact that Pd/C is recyclable, this reduction method offers undoubted advantages in terms of cheapness, practically and productivity as compared to all other methods known from literature.

The key reaction in the synthesis of (R)-3,4-dimethoxyamphetamine (3) are the condensation of dimethoxy-phenyl-acetone (12) with a chiral amine, and namely (R)-α-methyl-benzylamine (13) with the corresponding imine, [2-(3,4-dimethoxyphenyl)-1-methyl-ethylidene]-(1-phenylethyl)-amine (14) being formed and the diastereo-selective reduction of the latter by hydrogenation, into N-α-phenyl-ethyl-3,4-dimethoxy-amphetamine {or [2-(3,4-dimethoxyphenyl)-1-methyl-ethyl]-(1-phenyl-ethyl)-amine} (15).

Said synthesis was developed by D. E. Nichols et al. ("J. Med. Chem.", 1973, 16, 480–48 and U.S. Pat. No. 4,000, 197, of 12.28.1976) and was applied to the chiral synthesis of several methoxylated amphetamines, including (S)-3,4-dimethoxy-amphetamine, which is an enantiomer of (3). In U.S. Pat. No. 4,000,197, the synthesis of the iminic intermediate is carried out in benzene under refluxing conditions during 24 hours with formed water being simultaneously azeotroped off; the hydrogenation is carried out with Raney-Nickel as the catalyst, in absolute ethanol under medium-pressure hydrogen (3 atm of H₂). The N-α-phenyl-ethyl-3,4-dimethoxy-amphetamine (15) intermediate is isolated as hydrochloride salt, by crystallization in aqueous acetone or acetone/isopropanol blend, in moderate yield (relatively to dimethoxy-phenyl-acetone), of 48%.

In the application of such a method, some important modifications were incorporated by us which allowed us to considerably increase the process yield, up to 80%.

First of all, in the condensation reaction of phenyl-acetone (12) and (R)-α-methyl-benzylamine (13), benzene was replaced by cyclohexane, a much less toxic solvent. Furthermore, the required time for imine (14) formation was drastically reduced from 24 down to 5 hours (still under refluxing conditions), thanks to the addition of catalytic amounts of p-toluene-sulfonic acid which with (R)-α-methyl-benzylamine (13), present in a slight excess, supplies the corresponding salt (R)-α-methyl-benzyl-ammonium tosylate (13a), which is the actual catalyst.

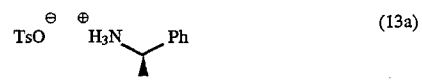

Also such a catalyst can be quantitatively recovered at reaction end, by filtration from cyclohexane, and indefinitely re-used. We furthermore observed that imine (14) is a rather unstable intermediate, because it is easily oxidized by atmospheric oxygen, at the methylene moiety between the iminic and arylic groups, into the corresponding α-keto-imine (14a)

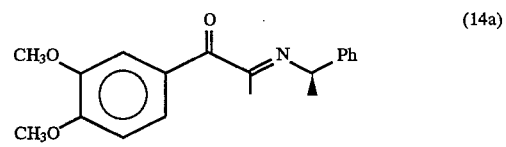

Such an oxidation is relatively fast: during the course of reaction (14a) it may even reach levels of 12–14% and can considerably increase, even up to 40%, if the solution of the imine is stored at room temperature in the presence of air. This byproduct is nearly quantitatively suppressed (<1%) by carrying out the reaction under an inert blanketing atmosphere (i.e., nitrogen or argon) and in the presence of catalytic amounts of a radical inhibitor, such as, e.g., 2,6-di-tert.-butyl-p-cresol.

We finally observed that also the temperature at which the reaction is carried out, as well as the concentrations of the reactants are also important: in fact, when toluene is used instead of cyclohexane (boiling point 110° C. instead of 80° C.), another impurity is formed in an amount of the order of magnitude of 8–9% which, on analysis by mass spectrometry, resulted to be a dimer with a molecular weight of 473, resulting from the condensation of two imine molecules followed by the cleavage of α-phenyl-ethyl-amine, having the following structure:

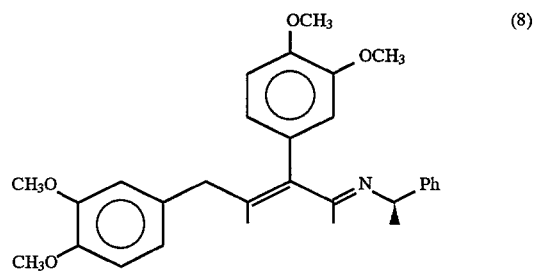

The amount of such a dimer increases with increasing reactant concentrations-and also when the process is carried out in the presence of an excess of (R)-α-methyl-benzyl-imine; therefore, the condensation seems to be base-catalized, with the benzyl carbanion being formed which adds up to the iminic moiety of another molecule: in any case, when the reaction is carried out in cyclohexane as the solvent, the level of such an impurity decreases under 1%.

By making resort to all of these measures, imine (14) results to be formed in a nearly quantitative yield (<98% by GLC).

The diastereo selective hydrogenation is carried out by using Raney-Nickel as the catalyst, in an analogous way to as taught by U.S. Pat. No. 4,000,197, and is highly stereoselective: the ratio of both diastereomers, i.e., (R,R)- and (S,R)-N-α-phenyl-ethyl-3,4-dimethoxy-amphetamine (15) and (15a)

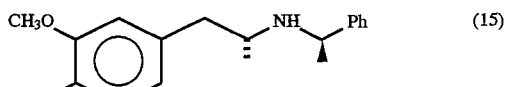

(R,R)

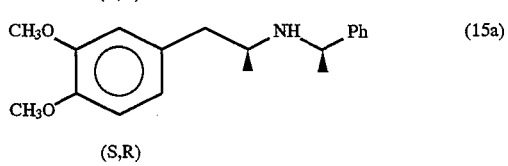

(S,R)

to each other depends on the solvent used in the reduction and increases with increasing solvent polarity: the results obtained in alcoholic solvents were as follows:

| SOLVENT | (R,R,)/(S,R) RATIO |
| --- | --- |
| Methanol | 97:3 |
| Absolute ethanol | 96:4 |
| Isopropanol | 94:6 |

Also the reduction rate is proportional to solvent polarity, and is maximal in methanol.

Using palladium on charcoal instead of Raney-Nickel leads to a sharp decrease of the ratio of (R,R):(S,R) down to 80:20; as well as, the reduction of imine (14) with sodium borohydride in ethanol is poorly stereoselective (ratio 70:30).

In the present invention, therefore, the reduction of imine (14) is carried out in methanol rather than in ethanol, as taught in U.S. Pat. No. 4,000,197, with a light increase in diastereoselectivity.

(R,R)-N-α-phenyl-ethyl-3,4-dimethoxy-amphetamine (14) is isolated by filtering off Raney-Nickel and distilling off methanol: the catalyst and the solvent can then be recycled to subsequent runs. The amphetamine product is then purified by dissolving it in isopropanol and acidifying the solution with concentrated aqueous hydrochloric acid or with hydrogen chloride in isopropanol; the hydrochloride (15) is isolated in a yield of 70–75% when aqueous hydrochloric acid is used and of 75–80% when hydrogen chloride in isopropanol is used: yields are therefore much higher than as reported in U.S. Pat. No. 4,000,197, which mentions a yield of 48%. The purity of hydrochloride product is of more than 98.5% (GLC): the (S,R)-diastereomer (15a) is present in amounts which are always lower than 1.0% (generally comprised within the range of from 0.5 to 0.7%). (R,R)-N-α-phenyl-ethyl-3,4-dimethoxy-amphetamine hydrochloride (15) can be possibly recrystallized from a suitable solvent (e.g., ethanol), with an extremely pure product being obtained (purity of >99.8% by-GC): however, in the synthesis of (R)-3,4-dimethoxy-amphetamine (3), such a recrystallization is not carried out.

(R)-3,4-dimethoxy-amphetamine hydrochloride (3) is then synthetized from intermediate (15) by hydrogenolysis of phenyl-ethyl moiety: the procedure is essentially followed which is disclosed in U.S. Pat. No. 4,000,197, by operating in methanol with palladium 10%/charcoal under a pressure of 4 atm of $H_2$, at a temperature of 40° C. the reaction is normally complete after 24 hours. (R)-3,4-dimethoxyamphetamine hydrochloride (3) is isolated, after filtering off the catalyst (which too is recyclable) and distilling off methanol, by crystallization from isopropanol, in a yield of 87–92%.

Amphetamine (3) displays an extremely good analytical purity (>99.5% by GLC and/or HPLC) and contains a level of (S)-3 enantiomer of less than 1.0% (chiral HPLC).

All characteristics resulted to be in accordance with published data and the optical rotary power is slightly higher than as reported in U.S. Pat. No. 4,000,197 ($[\alpha]_D^{20}$=−23.5° versus −23.1°).

Synthesis and resolution of (R)-3-chloromandelic acid

Racemic 3-chloromandelic acid is an intermediate which is presently found on the market at a relatively high price: industrially, it is prepared by following the classic synthesis route for mandelic acid by starting from corresponding benzaldehyde, via cyanohydrin:

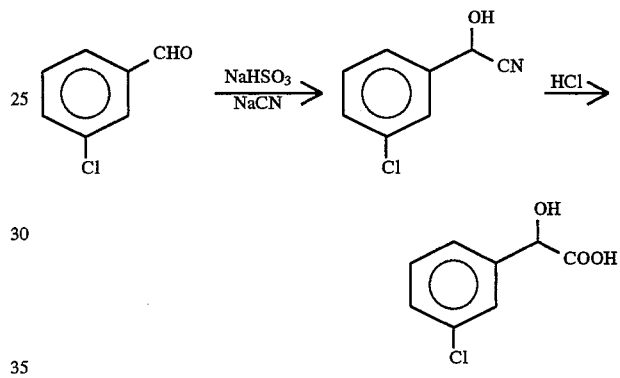

In technical literature also several modifications to this synthesis are reported, according to which a protected (o-acetyl, o-trimethylsilyl, and so forth) cyanhydrin is first formed, which is then hydrolysed in the second step.

A synthesis furthermore exists (A. Merz, "Synthesis", 1974, 724–725) which is carried out under phase transfer conditions in which the mandelic acids are prepared by reacting benzaldehyde with the dichlorocarbene generated in situ from chloroform and aqueous sodium hydroxide: a 2-chloro-aryl-acetyl chloride is formed which is then hydrolysed in the reaction media, yielding mandelic acid:

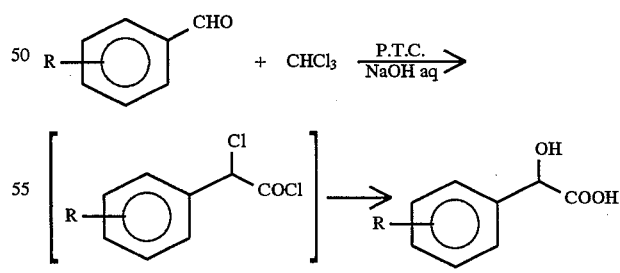

Unfortunately, such a synthesis only takes place with good yields when R is a n electron-donor group (H, $CH_3$, $OCH_3$): in the case of 3-chloromandelic acid, the yields are rather low.

The high cost of 3-chloromandelic acid is essentially due to the matter of fact that raw material 3-chlorobenzaldehyde and in general all 3-chlorobenzene derivatives are difficultly synthetized and relatively expensive: therefore, a synthesis was developed which starts from 3-chloro-bromobenzene, a relatively cheap raw material; such a synthesis is shown in following Scheme II: it uses published reactions reported for analogous compounds, not applied in the past to the synthesis of the above said acid.

3-Chloro-bromo-benzene is converted into the corresponding Grignard reactant 3-chloro-phenyl-magnesium bromide, which is then reacted under low temperature conditions (–10° C.) with acetyl chloride, in the presence of copper-(!) chloride as the catalyst, yielding raw 3-chloro-acetophenone (16), in quantitative yield and with a purity of >85% (GLC) (see, e.g., Org. Synth., 66, 116–120). 3-Chloro-acetophenone (16) is chlorinated with sulfuryl-chloride in acetic acid yielding 3'-chloro-2,2-dichloro-acetophenone (17) which is not isolated, but is hydrolysed in situ into the corresponding ketoaldehyde which, under basic conditions, undergoes a dismutation into 3-chloromandelic acid (9) (internal Cannizzaro reaction, see "Org. Synth. Coll.", Vol. 3, 538–541).

The acid (9) is isolated by acidification of the reaction mixture, extraction and crystallization from a suitable solvent, with an overall yield of 60–65% (based on 3-bromo-chloro-benzene) and a purity of >98.5% (GLC).

To prepare the (R)-3-chloromandelic acid enantiomer (R)-(9), an enzymatic process exists in literature (see European Patent Application EP 449,648 filed on Oct. $2^{nd}$ 1991), which uses the enantioselective hydrolysis of the corresponding racemic cyanohydrin [ArCH(OH)CN], catalyzed by a plurality of enzymes: however, this method departs from the process according to the present invention.

As far as we know, furthermore one single method exists for resolving the racemic mixture, based on use of (-)-ephedrine as the resolving agent (see A. Collet et J. Jacques, "Bull. Soc. Chim. Fr.", 1973, 12, 3330–3334): according to such a method, (R)-3-chloromandelic acid (9) is isolated in a yield of 29% based on theoretical yield (i.e., based on 50% of enantiomer of (R)-enantiomer present in the racemic blend).

In the present invention, an original resolution method is introduced (Scheme III) which uses, as the resolving agent, (R)-α-methyl-benzyl-amine (13) [(R)-FEA], already used in the synthesis of (R)-3,4-dimethoxy-amphetamine (3); as such a resolving agent is available in the form of both enantiomers at a same price, the method can be also used to resolve the (S)-enantiomer.

Furthermore, the resolution of (R) acid is carried out in water and in such a reaction media, we succeeded in racemizing in situ the (S)-enantiomer, which can be therefore recycled to a subsequent resolution cycle: furthermore, by means of simple extraction operations, also (R)-α-methyl-benzyl-amine (13) can be recovered, which too is recyclable.

SCHEME II

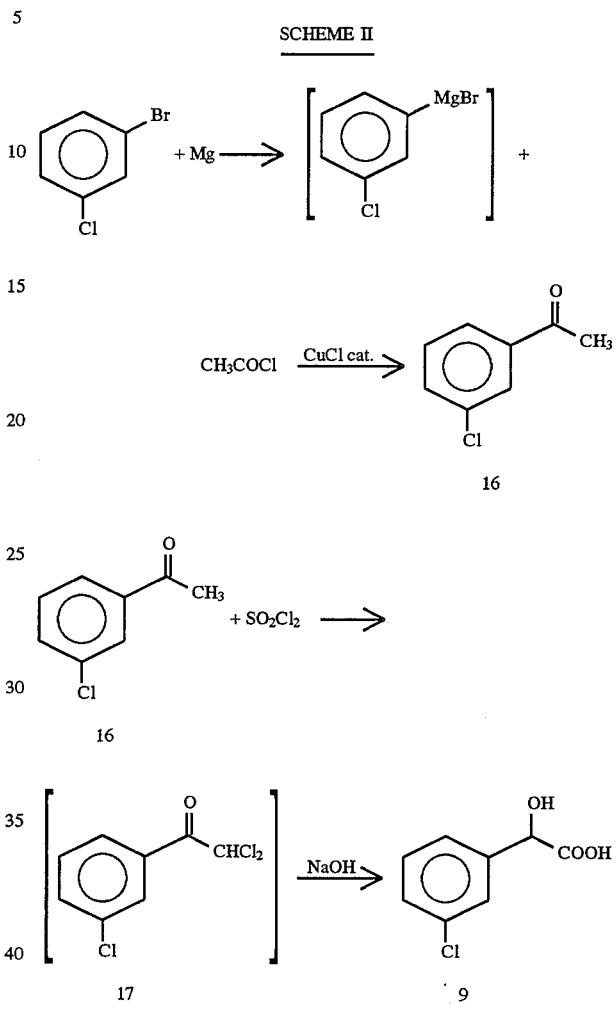

SCHEME III

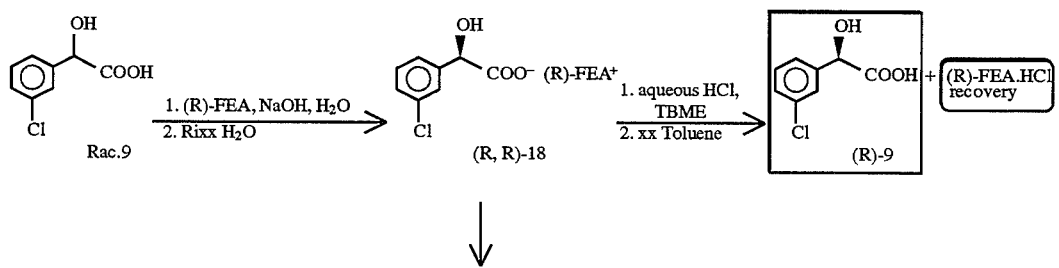

↓

-continued
SCHEME III

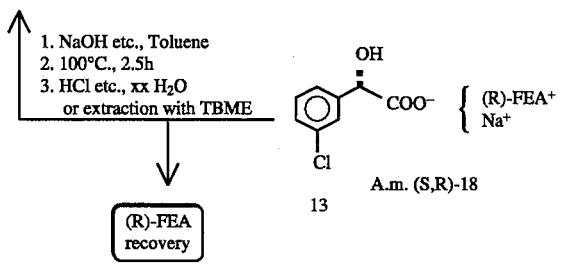

The proposed method implies crystallizing (R,R)-α-methyl-benzylammonium-3-chloromandelate salt (18) in water, using a deficient amount of resolving agent (13) relatively to the racemic acid (9) and compensating for the base lack with sodium hydroxide. The raw (R,R)-salt (18) is isolated in a yield of 85% relatively to the theoretical value and with an (R,R)/(S,R) ratio of 86:14 (chiral HPLC analysis): the (R,R)-salt is recrystallized from water with the (R,R)-salt (18) being obtained in a yield of 66% relatively to the theoretical yield [33% based on racemic acid (9)] and with an (R,R)/(S,R) ratio of 98:2.

(R)-3-chloromandelic acid (9) is easily obtained by starting from (R,R)-salt (18) by acidification with an aqueous acid, extraction with a suitable solvent and crystallization: the acid is quantitatively recovered from salt (18) with a chemical purity higher than 99% and an optical purity of 98% (96% e.e.). From acidic aqueous phase (R)-methyl-benzyl-amine (13) can be recovered by means of basification, extraction and vacuum distillation.

As compared to the resolution method using (-)-ephedrine, (R)-3-chloromandelic acid (9) is obtained in a more than twice as large yield (66% versus 29% of theoretical value), even if its optical purity is slightly lower, however, more than enough for the subsequent synthetic steps.

As previously mentioned, (S)-3-chloromandelic acid, contained in crystallization mother liquors in salt form with (R)-methyl-benzyl-amine and sodium salt (see Scheme III) can be racemized and recovered.

Adding an excess of aqueous sodium hydroxide allows (R)-methyl-benzyl-amine (13) to be released and then extracted by means of a suitable solvent and purified by distillation; the sodium salt of (S)-acid is racemized by simply heating the strongly basic aqueous solution (this racemization is probably due to a nucleophilic substitution of hydroxyle anion linked to the m-carbon relatively to carboxylate moiety, rather than to an improbable removal of proton from said carbon, unfavoured by the presence of carboxylate moiety in α-position); 3-chloromandelic acid (9) is then isolated either by direct crystallization from aqueous medium by addition of inorganic acid, or by extraction with a suitable solvent from acidic aqueous phase. In both cases, the recovery rate is rather high (62–65%, relative to a theoretical content of 67%, see Scheme III).

The purity of recovered racemic acid is generally of >98.5% (mainly when it is isolated by crystallization) and is high enough to allow said acid to be recycled to a subsequent resolution cycle.

Therefore, the method introduced herein is characterized by a good cheapness, deriving from racemization of undesired enantiomer, recovery of resolving agent and use of cheap raw materials and solvents, which too can be recovered and recycled; the procedure is also a very simple one and this resolution process could be also applied to other substituted mandelic acids.

Synthesis of (R,R) -oxazolidinone (1)

The synthesis of [R-(R*,R*)]-5-(3-chlorophenyl)-3-[2-(3,4-dimethoxyphenyl)-1-methyl-ethyl]-oxazolidin-2-one (1) is carried out according to Scheme IV and implies the following reactions:

1. acetylation of (R)-3-chloromandelic acid (9) with (R)-O-acetyl-3-chloromandelic acid being formed which is converted into the corresponding acyl chloride, i.e., (R)-O-acetyl-3-chloromandeloyl chloride (19);
2. coupling reaction of chloride (19) with (R)-3,4-dimethoxy-amphetamine hydrochloride (3), with the novel compound [R-(R*,R*)]-2-(3-chlorophenyl) -N-[2-(3,4-dimethoxyphenyl)-1-methyl-ethyl]-2-acetoxy-acetamide (20) [(R,R)-acetoxyamide] being formed;
3. de-acetylation of intermediate (20) to yield the novel compound [R-(R*,R*)]-2-(3-chlorophenyl)-N-[2-(3,4-dimethoxy-phenyl)-1-methyl-ethyl]-2-hydroxy acetamide (21), [(R,R) -hydroxy amide];
4. reduction of the amidic moiety of intermediate (21) with the corresponding phenethanolamine, [R-(R*, R*)]-1-(3-chlorophenyl)-2-[2-(3,4-dimethoxyphenyl)-1-methyl-ethylamino]ethanol (5) being obtained;
5. formation of (R,R)-oxazolidinone (1) by reaction of phenethanolamine (5) (β-amino-alcohol) with a suitable reactant.

Preparation of (R)-O-acetyl-3-chloromandeloyl chloride (19) is carried out according to a well-known published synthesis (see "Org. Synth. Coll.", p. 12–13) and recently applied also on optically active mandelic acid (see E. J. Corey, "J. Am. Chem. Soc.", 1986, 108, 7114–7116): it implies the initial acetylation with acetyl chloride in a suitable solvent and the subsequent formation "in situ" of acyl chloride with thionyl chloride.

These reaction steps proceed in a nearly quantitative yield and with a complete absence of byproducts: however, it is important that they are run under controlled conditions in order to prevent the reactant from undergoing a partial racemization, which is easily observed in the subsequent coupling step with (R)-3,4-dimethoxy-amphetamine (3) in which together with (R,R)-acetoxyamide (20), also the undesired (S,R)-diastereomer (20)

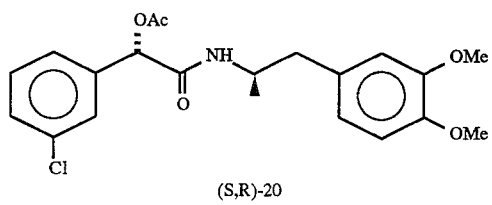

(S,R)-20 is obtained.

The partial racemization of (R)-O-acetyl-3-chloromandeloyl chloride (19) depends on temperature and occurs when the process is carried out at higher temperatures than 40° C. both in acetylation and in acyl chloride formation step: in fact, in both said steps, two dehydrating reactants (acetyl chloride and tionyl chloride) are used and at high temperatures they are likely to dehydrate (R)-3-chloromandelic acid (9) or (R)-O-acetyl-3-chloromandelic acid into the corresponding ketene, with consequent loss of chirality. The formed ketene is obviously reactive with any nucleophiles, like acyl chloride.

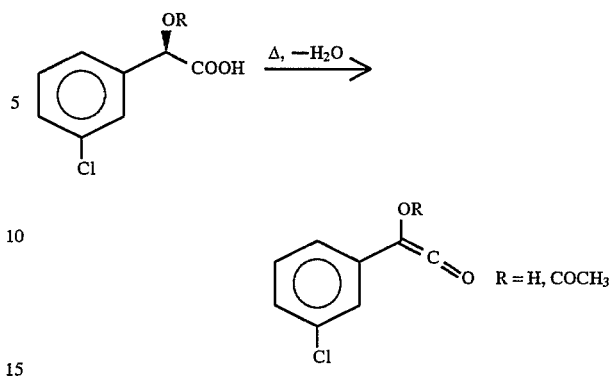

R = H, COCH3

According to the present method, the acetylation is therefore carried out in methylene chloride at 27°–30° C., and the acyl chloride formation is carrfed out under refluxing conditions (approximately 40° C.).

Also the reaction with (R)-3,4-dimethoxyamphetamine hydrochloride (3), which apparently is a normal amidation

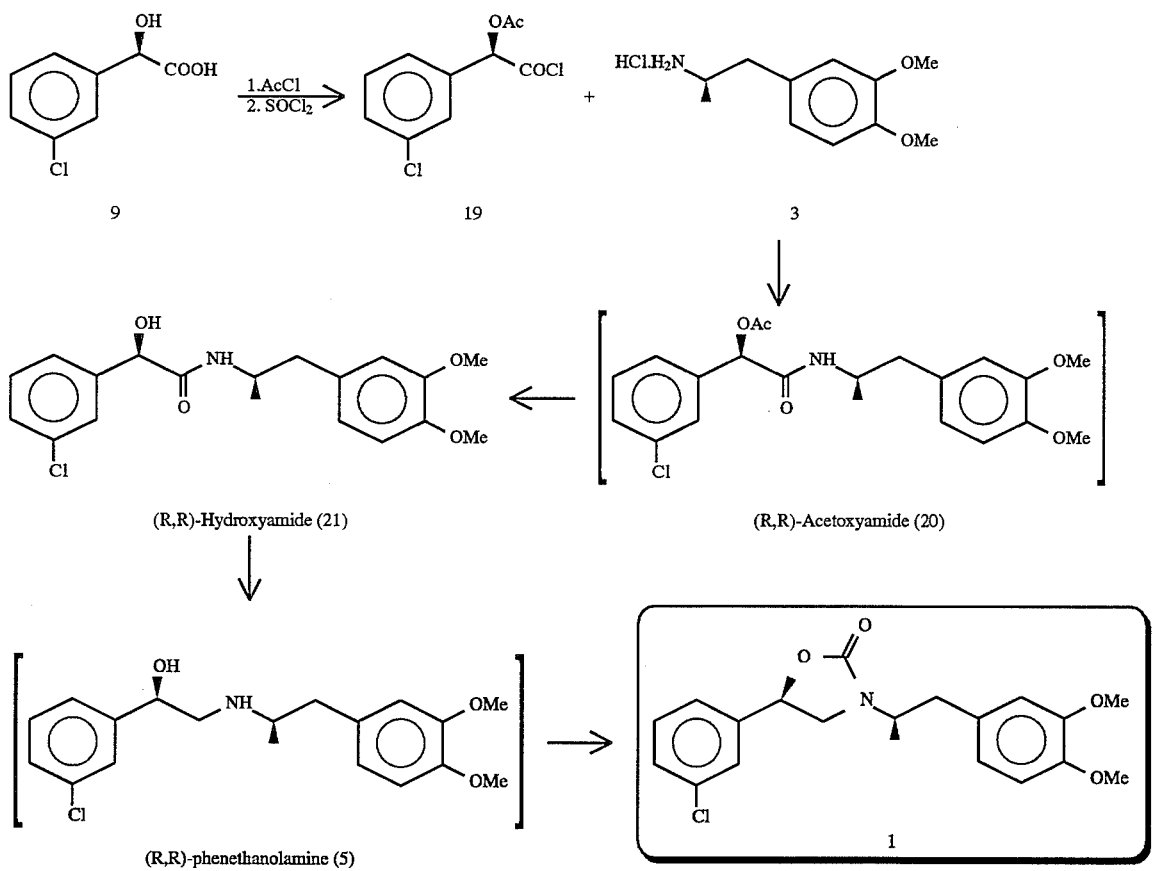

reaction, must be carried out with special cares in order to prevent the above said racemization from occurring, which in this case depends on the pH value of the reaction media and on the base type used in order to neutralize the developed hydrochloric acid.

A partial racemization was observed when as bases triethylamine or pyridine were used; both of them are well-known reactants capable of forming ketenes from the corresponding acyl chlorides:

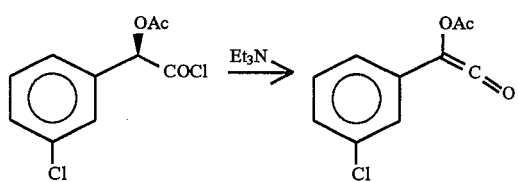

Such a reaction is therefore carried out according the customary procedure by Schotten-Baumann under controlled pH conditions, lower than 7.5. In greater detail, a certain amount of an aqueous solution of sodium hydrogencarbonate is added to a suspension of amphetamine hydrochloride (3) in methylene chloride at 0°–5° C. in order to cause a fair amount of amphetamine base to be released; then (R)-O-acetyl-chloromandeloyl chloride (19) and a solution of sodium carbonate are added dropwise simultaneously in order to constantly keep the pH value at a nearly neutral value (pH 6–7.5).

In such a way, the amidation reaction is nearly quantitative and the level of (S,R)-acetoxyamide diastereomer is generally lower than 4.0%.

The (R,R)-acetoxyamide intermediate (20) is isolated by simply separating it from the organic phase and concentrating to dryness.

The deacetylation of intermediate (20) into (R,R)-hydroxyamide (21) is carried out under basic conditions, in an alcoholic solvent in the presence of a catalytic amount of sodium hydroxide: in such a way, a fast transesterification reaction is obtained and the hydroxy-amide is isolated in high yields (86–90%) by simply adding acetic acid in order to neutralize the reaction media, and water, as the precipitating solvent.

The purity of (R,R)-hydroxyamide (21) is generally high, because the sole detected impurity is the (S,R)-diastereomer (21), present at a level of 3–3.5%.

It is interesting to observe that both intermediates (20) and (21) are stable in the basic reaction media although they, and in particular intermediate (20), contain the proton in α-position to carbamidic carbon with a rather acidic character, because it is linked in fact to 3 electron attractant moieties (carboxyamide, acetoxy and phenyl moieties).

This feature supports the hypothesis that the previously observed racemization is precisely associated with partial ketene formation from the corresponding acyl chloride.

The conversion of (R,R)-hydroxyamide (21) into (R,R)-phenethanolamine (22) implies the reduction of carboxyamide moiety into a secondary amine having a β-hydroxy group.

Such a reduction requires a particularly strong reducing agent because the amidic group is one from most difficult groups to be reduced.

Reduction with lithium-aluminum hydride, one of most used reactants for such a purpose, requires relatively harsh conditions (refluxing tetrahydrofuran) unfortunately leading to partial de-halogenation of 3-chloro-phenyl ring.

The reduction with ®Vitride [sodium (bis-(2-methoxyethoxy)-aluminum dihydride] requires even harsher conditions, because such a reductant proved to be less effective than LiAlH$_4$: such conditions lead to a partial dehydration of phenethanolamine (22) with the corresponding enamine (or tautomeric imine) being formed:

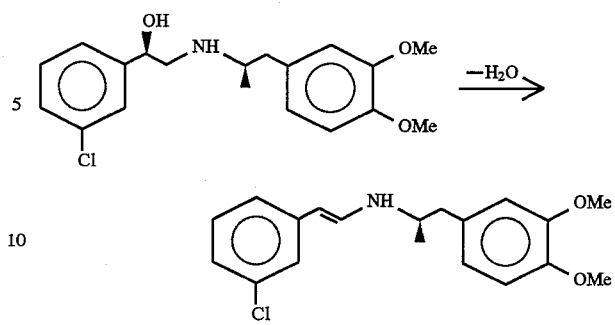

The sodium borohydride/acetic (or trifluoroacetic) acid reactant, with sodium acetoxy- (or trifluoroacetoxy-) borohydride being formed "in situ" [see the review by G. W. Gribble, "Org. Prep. Proc. Int.", 17 (4–5), 317–384 (1985)], on the contrary, demonstrated to be at all ineffective to perform such a reduction.

Another reductant largely used in such reductions is diborane, which generally leads to high amine yields, it being furthermore at all non-reactive towards aromatic halides (see the review by C. F. Lane, "Chem. Rev.", 1986, 76, 773–799).

Diborane-tetrahydrofuran complex (in diluted THF solution) proved to be an extremely good reductant for hydroxyamide (22): the reduction resulted to be quantitative and very clean, practically with no byproducts being formed: unfortunately, a possible industrial use of such a reactant seems to be rather problematic owing to the dangerousness of said reactant, deriving from its highly pyrophoric character.

At all analogous results were anyway obtained with borane-dimethylsulfide complex, a less pyrophoric, easier to handle liquid reactant than diborane in THF (see H. C. Brown et al., "Synth.", 1981, 996–997 and "J. Org. Chem."1982, 47, 3153–3163); unfortunately, such a reactant suffers from the drawback of being malodorous and releasing, at reaction end, a stoichiometric amount of dimethyl sulfide, an also malodorous, very volatile liquid substance, which requires a suitable treatment, when used on an industrial scale, to prevent environmental problems.

Reducing the hydroxy amide (20) with borane-dimethylsulfide in tetrahydrofuran leads to the quantitative formation of phenethanolamine (21) under conditions of complete absence of byproducts and total absence of racemization at both chiral centres: the obtained product after work-up is a low-melting solid substance which is directly used in the end reaction without any further purification.

In order to avoid using the above said reactant, diborane can also be generated "in situ", by treating sodium borohydride with a suitable acidic reactant. The best results were obtained by operating in tetrahydrofuran and using, as the Lewis acid, the etherated boron trifluoride complex or sulfuric acid or methane-sulfonic acid (see also H. C. Brown et al. "J. Am. Chem. Soc." 1960, 82, 4233–4241; A. Abiko and S. Masamune, "Tetr. Lett." 1992, 33, 5517–5518): although they are advantageous from both industrial and financial viewpoints, such reactions lead to the formation of phenethanolamine (21) in good yields, but contaminated by the presence of small amounts of some byproducts.

Other sodium borohydride activators for diborane production [for example, trimethyl-silyl chloride, phosphorous oxychloride, titanium-(IV) chloride] did not yield any reactions, probably due to the presence of the hydroxy group in Q-position relatively to the amidic system, which may react with the above said reactants.

The conversion of phenethanolamine (21) into (R,R)-oxazolidinone (1) can be advantageously carried out by using several reactants.

The most used reactants at present are: phosgene and relevant phosgenating agents trichloromethyl chloroformate ("diphosgene") and bis-(trichloromethyl) carbonate ("triphosgene"); dialkyl carbonates and alkyl chloroformates; more "exotic" reactants, such as carbonyl diimidazole and 1,1'-(carbonyl-dioxy)-dibenzotriazole, the first of which was used by J. Bloom in U.S. Pat. No. 5,061,727.

Some of these reactants show some drawbacks:

phosgene is a highly toxic gas, useable with great difficulty on an industrial scale;

using dialkyl carbonates and/or alkyl chloroformates requires relatively harsh conditions (basic media and/or high temperatures), probably not compatible with our substrate (possible racemization of Q-carbon from the hydroxy group);

carbonyl diimidazole and similar reactants are rather expensive and generally find a limited usage to small-scale reactions.

We therefore focused our attention onto using trichloromethyl chloroformate ClCOOCl$_3$, "diphosgene", an easily and cheaply prepared reactant by photochlorination of methyl chloroformate.

Such a reactant is a relatively high-boiling liquid substance (boiling point=128° C.), stable at room temperature; although it is generally regarded as being a reliable and safe alternative to phosgene, it must anyway be used cautiously because, upon contacting a whatever nucleophile (and therefore also water), it may release fairly large amounts of phosgene (see "Chem. Eng. News" 1993, 8$^{th}$ February, page 4). However, on an industrial scale, it can be prepared in large amounts and used in line, in closed loop.

Trichloromethyl chloroformate displays a reactivity which is similar to phosgene and it was recently used by some researchers of Smith, Kline & French precisely to prepare oxazolidones from β-aminoalcohols (L. N. Pridgen et al., "J. Org. Chem."1989, 54, 3231–3233). In this paper the cyclization is carried out at low temperature (from –10° C. to +20° C.) under phase transfer conditions, with the reaction media being kept constantly basic (pH=9–11) and proceeds with very good yields on amino-alcohols derived from natural α-aminoacids.

When we repeated such a method, we did not achieve the expected results and observed low conversion rates also when we used an excess of diphosgene: this matter of fact is probably due to the presence of two secondary rather than primary—as in cited reference—aminic and hydroxy moieties, which cause phenethanolamine (21) to become less reactive. Furthermore, as we wanted to avoid basic reaction conditions and water presence, we thought of using an acceptor of hydrochloric acid, a product of the reaction, not displaying basic charactertistics. According to the present invention, we decided to use an epoxide which is a very reactive species with inorganic acids and with released hydrochloric acid forms the corresponding chlorohydrin, an absolutely neutral species.

Actually, the presence in the reaction media of butylene oxide (1,2-epoxy-butane) in a slight excess over trichloromethyl chloroformate allows (R,R)-oxazolidinone (1) to be synthetized efficiently: the reaction proceeds at room temperature or at a slightly higher than room temperature, and is complete, and quantitative, within short times, with no impurities being formed. The slight excess of trichloromethyl chloroformate is decomposed by means of the addition of aqueous ammonium hydroxide (under such conditions, the oxazolidinone is stable and does not undergo isomerization) and the product is isolated by simply concentrating the reaction mixture to residue and is purified by crystallization from a suitable solvent.

The desired product is obtained in yields of 83–88% [based on R,R-hydroxyamide (20)] and displays a high purity level, generally higher than 99.0% (of 99.5% on an average), with a content of undesired (S,R)-diastereomer (1) lower than 0.5% (0.2% on an average).

The overall yield of this new synthesis of oxazolidinone (1) [from (R)-3,4-dimethoxyamphetamine (3) and (R)-3-chloromandelic acid (9)] is of round 75–77% and is therefore higher than as obtained by J. D. Bloom by means of the method via (R)-3-chlorostyrene oxide, previously discussed: furthermore, using carbonyl-diimidazole in oxazolidinone synthesis is avoided, with a considerable saving in raw materials costs.

In order to better understand the characteristics and advantages of the present invention, non-limitative, exemplifying embodiments thereof are disclosed in the following.

EXAMPLE 1

(3,4-Dimethoxyphenyl)-2-nitropropene (11)

A mixture of veratraldehyde (200 g, 1.20 mol), ammonium acetate (94.0 g, 1.22 mol) nitroethane (400 ml, 418 g, 5.57 mol) and toluene (200 ml) is refluxed for 2 hours and thirty minutes, with ternary azeotrope toluene/nitro ethane/water being distilled off and formed water being separated. The red solution is cooled down to about 40° C. and is concentrated to residue at 40°–50° C./20 mbar.

The residue, a deep red oil, is dissolved in hot 90% aqueous methanol (800 ml) and is crystallized at a temperature of 0°–5° C. during 2–3 hours. The product is isolated by filtration, the filter cake is washed with 90% methanol (200 ml) and is dried to constant weight, with 225–234 g of yellow crystals of solid (3,4-dimethoxyphenyl)-2-nitropropene (11) being obtained (yield 84–87%), with a GC purity of higher than 99.5%. (NMR, MS) analyses are in agreement with published data.

EXAMPLE 2

3,4-Dimethoxyphenyl-acetone (12)

(3,4-Dimethoxyphenyl)-2-nitropropene (11) (200 g, 0.90 mol), palladium 10%/charcoal (10.0 g, either fresh or recycled), methanol (750 ml), water (220 ml) and sulfuric acid (96%, 28 ml) are charged to a steel autoclave thermostatted at 15° C.

The reaction mixture is hydrogenated under 4 atm of hydrogen at 17°–20° C. during 2–4 hours until hydrogen consumption comes to an end. The autoclave is discharged and the catalyst is filtered off and washed with methanol; the reaction mixture is concentrated under vacuum, at 40°–45° C./25–30 mbar, with methanol being distilled off. To the resulting aqueous mixture, toluene (250 ml) and aqueous formaldehyde at 40% w/v (250 ml) are added, and the resulting mixture is kept stirred for 1 hour at 20°–25° C. The organic phase is separated and the aqueous phase is extracted once more with toluene (250 ml); the combined organic phases are washed with water (2×250 ml) until the wash liquors reach a pH value of >4; they are then concentrated to residue at 50° C./20 mbar. The yellow-orange oil containing raw 3,4-dimethoxy-phenyl-acetone (12) [theoretical amount 174 g], having a purity of 98.5–99.0% (GC), is used without any further purifications; it can anyway be distilled, with that fraction being collected which distils at 108°–110° C./0.1 mbar (148–156 g, yield 85–90%].

(NMR, MS) analyses yield consistent results with published data.

EXAMPLE 3

(R)-[2-(2,3-Dimethoxyphenyl)-1-methyl-ethylidene] -1-(phenyl-ethyl)amine (14)

A mixture of raw 3,4-dimethoxyphenylacetone (12) (theoretical amount 174 g; 0.90 mol), (R)-N-α-methyl-benzylamine (13) (130 g, 1.07 mol), 2,6-di-tert.-butyl-p-cresol (3.5 g, 0.016 mol), p-toluene-sulfonic acid (8.4 g, 0.044 mol) and cyclohexane (1500 ml), is kept heated under refluxing conditions for 5 hours under an inert atmosphere (nitrogen or argon) with water being distilled azeotropically as it is released. The reaction mixture is cooled down to 15° C. and the precipitate, constituted by (R)-N-α-methyl-benzyl-ammonium tosylate, a white crystalline solid (13 g), is filtered off and is recycled to subsequent runs, instead of p-toluene-sulfonic acid.

The reaction mixture is concentrated to residue at 40°–45° C./20 mbar and a thick yellow oil is obtained which contains raw (R)-[2-(3,4-dimethoxyphenyl)-1-methyl-ethylidene]-1-(phenyl-ethyl)amine (14) (theoretical 267 g), having a GC purity of 95–96%, which is used as such, without any further purifications, in the subsequent reaction.

EXAMPLE 4

(R,R)-[2-(3,4-dimethoxyphenyl)-1-methyl-ethyl]-1-(phenyl-ethyl) -amine (15)

Raw (R)-[2-(3,4-dimethoxyphenyl)-1-methyl-ethylidene] -1-(phenyl-ethyl)-amine (14) (theoretical 267 g), methanol (900 ml) and Raney-Nickel (80 g, carefully washed with methanol by decantation) are charged to a steel autoclave thermostatted at 25° C. The resulting mixture is hydrogenated under 4 atm of hydrogen until hydrogen consumption comes to an end (generally within a time of from 12 to 18 hours, according to whether fresh or recycled catalyst is used). The autoclave is discharged and the catalyst is filtered and washed with methanol. The solution is concentrated to residue at 40° C./20 mbar. The resulting yellow oil is dissolved in isopropanol (1000 ml) and 25% hydrochloric acid in isopropanol (240 ml) is added slowly, at 30°–35° C. until the pH value of the mixture reaches pH<3.

The suspension is kept stirred for 2 hours at 0° C.: the product is filtered off, is washed with cold isopropanol (3×80 ml) and is dried to constant weight, with (R,R)-[2-(3,4-dimethoxyphenyl)-1-methyl-ethyl]-1-(phenyl-ethyl)-amine hydrochloride (15) being obtained, a basic crystalline solid (230–240 g, yield: 76–80%) with a GC purity of 98.5–99.0%, containing 0.5–1.0% of (S,R)-diastereomer.

The analytical characteristics {melting point=213° C., $[\alpha]_D^{20}$ (C=2 MeOH)=+25.4°, NMR and MS spectra} are consistent with published data.

EXAMPLE 5

(R) -3,4-dimethoxyamphetamine (3) hydrochloride (R,R)-[2-(3,4-dimethoxyphenyl)-1-methylethyl]-1-(phenylethyl) amine (15) hydrochloride (200 g, 0.596 mol), palladium 10%/charcoal (20 g), and methanol (600 ml), are charged to a steel autoclave thermostatted at 40° C. The hydrogenation is carried out under 4 atm of hydrogen until hydrogen consumption comes to an end (generally during 20–24 hours). The autoclave is discharged and the catalyst is filtered off. The solution is concentrated to residue at 50° C./20 mbar. The resulting oil is dissolved in hot isopropanol (400 ml) and is crystallized at 0° C. for several hours: the product is filtered, washed with cold isopropanol (100 ml) and dried up to constant weight, with (R)-3,4-dimethoxyamphetamine (3) hydrochloride being thus obtained in the form of a crystalline white solid (119–125 g, yield: 86–90%, having a purity of >99.5% (by GC and HPLC) and having a content of (S)-enantiomer comprised within the range of from 0.5 to 0.8% (as determined by chiral HPLC analysis).

The analytical characteristics {melting point=140° C., $[\alpha]_D^{20}$ (C=2, H$_2$O)=−23.5°, NMR and MS spectra} are consistent with published data.

EXAMPLE 6

3'-Chloroacetophenone (16)

Magnesium chips (24.3 g, 1.00 mol) and tetrahydrofuran (300 ml) are charged to a flask of 2 liters of capacity, under an inert atmosphere.

To such suspension a solution of 3-bromochlorobenzene (194.5 g, 1.00 mol) in toluene (700 ml) is added dropwise, during 1.5 hours, at 36°–38° C. The reaction mixture is kept with stirring for 1 hour at 35°–25° C.

Copper-(I) chloride (5.0 g, 0.50 mol) and tetrahydrofuran (300 ml) are charged to another flask of 2 liters of capacity, under an inert atmosphere.

The reaction mixture is cooled down to −15° C. and acetyl chloride (102 g, 1.30 mol) is added to it.

The previously prepared 3-chlorophenyl-magnesium bromide solution is then added dropwise during 3–4 hours, with temperature being kept comprised within the range of from −15° C. to −10° C. The reaction mixture is kept stirred for 1 hour at −15° C., and 2 M hydrochloric acid (500 ml) is slowly added thereto. The reaction mixture is heated up to 20° C., the aqueous phase is separated, and the organic phase is extracted with toluene (200 ml) and the combined organic phases are washed with 2M hydrochloric acid (500 ml), water (500 ml) and 5% aqueous sodium bicarbonate (500 ml).

The reaction mixture is concentrated to residue at 50° C./20 mbar, with a thick yellow oil being thus obtained (166 g, higher yield than theoretical yield due to the presence of residual toluene) which contains raw 3'-chloroacetophenone (16), having a GC purity comprised within the range of from 85 to 87%, which is used as such, without any further purifications

EXAMPLE 7

3-Chloromandelic acid (9)

Raw 3'-chloroacetophenone (16) (theoretical amount 166 g, 1.0 mol) is dissolved in acetic acid (160 ml); then, sulfuryl chloride (312 g, 2.30 mol) is dropwise added it during 1 hour at a temperature comprised within the range of from 30° to 35° C. The reaction mixture is heated up to and kept heated at 40° C. for 2 hours.

The reaction mixture is cooled down to 20° C. and is dissolved in water (300 ml) and ice (300 g). 3'-Chloro-2,2-dichloroacetophenone (17) is extracted with 1,2-dichloropropane (2×300 ml) and the organic phase is concentrated to residue at 40° C./20 mbar, with a yellow oil being obtained which is dropwise added during 2 hours to a solution of 10% sodium hydroxide (1.0 l), kept heated at 60°–65° C. The reaction mixture is cooled down to room temperature, is washed with toluene (100 ml), is acidified with concentrated hydrochloric acid (200 ml) at 30°–35° C. and is then extracted with t-butyl-methyl ether (2×300 ml).

The organic phase is concentrated to residue at 40° C./20 mbar, with raw 3-chloromandelic acid (9) 168 g, yield: 90%) being thus obtained. The product is crystallized by dissolving it in hot toluene (350 ml) and keeping the resulting mixture at 20° C. for several hours: the solid is filtered, is washed with toluene (150 ml) and is dried to constant weight, with 3-chloromandelic acid (9) (120 g, yield from 3-bromo-chloro-benzene: 63) being thus obtained a purity of 98.5–99.0% (as determined by GLC, silanized support).

The analytical characteristics {melting point=115° C., NMR and MS spectra} are consistent with published data.

EXAMPLE 8

(R,R)-α-Methylbenzylammonium-3-chloromandelate (18)

3-Chloromandelic acid (500 g, 2.69 mol) is suspended in water (1.5 l). A solution of sodium hydroxide (37.5 g, 0.94 mol) in water (500 ml) is added to it. (R)-N-α-methyl-benzylamine (212.5 g, 1.75 mol) is then dropwise at 30°–32° C. added to the reaction mixture: the resulting mixture is the heated up to 60° C. until a clear solution is obtained. The reaction mass is slowly cooled during 3 hours down to 25° C.; the reaction mass is kept stirred for several hours at 25° C. and then during 2 hours at a temperature of 18°–20° C.

The salt is filtered, is washed with water (200–300 ml) and is dried to constant weight (352 g, 85% of theoretical weight, (R)/(S) ratio=86:14). Raw (R,R)-α-methyl-benzyl-ammonium 3-chloromandelate (18) is recrystallized by dissolution in hot water (1400 ml) and slow cooling down to 20° C. The precipitate is filtered, washed with water and dried to constant weight, with pure (R,R)-α-methyl-benzyl-ammonium 3-chloromandelate (18) {273 g, yield 66% of theoretical yield, melting point=146°–150° C. $[\alpha]_D^{20}$ (C=2, MeOH)=–42.3°, (R)/(S) ratio =98:2}.

EXAMPLE 9

RS (Reference Standard) (R, R)-α-methylbenzylammonium 3-chloromandelate (18)

Pure (RR) salt (18) (25 g) is dissolved in hot denatured ethanol (100 ml). The solution is filtered by theorite and the salt is crystallized by slowly cooling down to 15° C.

The product is filtered, washed and dried, with 12.5 g of RS (R,R)-α-methylbenzylammonium 3-chloromandelate (18) being thus obtained {melting point=147°–151° C., $[\alpha]_D^{20}$ (C=2, MeOH)=–43.7°}.

Upon further crystallization no increases in melting point or optical power are observed.

EXAMPLE 10

(R)-3-chloromandelic acid (9)

(R,R)-α-methylbenzylammonium 3-chloromandelate salt (18) (270 g, 0.88 mol) is suspended in water (700 ml). 36% Concentrated hydrochloric acid (140 ml) is dropwise added to the suspension, with stirring, at 20°–25° C. until an acidic pH is reached, with a slightly yellow solution being thus obtained. To this solution t-butyl-methyl ether (550 ml) is added, and the reaction mixture is stirred for 15 minutes.

The organic phase is separated and the aqueous phase is re-extracted with t-butyl-methyl ether (550 ml); the combined organic phases are washed with water (200 ml) and concentrated to residue at 40° C./20 mbar. The solid residue is dissolved in hot toluene (500 ml) and crystallized at 0° C. for several hours; (R)-3-chloromandelic acid (9) is filtered, washed with cold toluene (100 ml) and dried up to constant weight (160 g, crystalline white solid; salt yield (RR)=98%).

The so obtained product has the following characteristics:
melting point=102°–103° C (lit., 103°–105° C.)
$[\alpha]_D^{20}$ (C=2, EtOH)=–111.4° (lit. –116° C.)
e.e.=96%
(R)/(S) ratio (by chiral HPLC)=>98:2
Analysis (GLC, silanized, % area)=99.5%.

EXAMPLE 11

Racemization of (S)-3-chloromandelic acid (9)

To the combined mother liquors from the first and second crystallizations of (R,R) salt (18), having a theoretic content of 335 g of (S)-3-chloromandelic acid (67% of the starting amount of 3-chloromandelic acid), a 30% solution of sodium 30 hydroxide (400 ml) is added. The resulting cloudy mixture is extracted with toluene (2×400 ml). From this organic phase (R)-α-methylbenzylamine can be recovered by concentration to residue and distillation.

The aqueous solution is refluxed for 2.5–3 hours: the racemization course is followed by polarimetric analysis, with refluxing being stopped when [α]=0° C.

The solution is cooled down to 20° C. and 36% concentrated hydrochloric acid (270 ml) is dropwise added until an acidic pH value is obtained, at a temperature comprised within the range of from 25°–30° C. The resulting suspension is cooled down to 0° C. for several hours: racemic 3-chloromandelic acid is filtered, washed with cold water and dried up to constant weight (290–300 g, corresponding to a recovering rate of 86–89% based on theoretical weight).

The recovered acid has the following characteristics:
$[\alpha]_D^{20}$ (C=2 EtOH)=0.0°
Analysis (GLC, silanized, % area)=99.3%
Melting point=113°–115° C.

EXAMPLE 12

(R)-O-acetyl-3-chloromandeloyl chloride (19)

(R)-3-chloromandelic acid (9) (80.0 g, 0.429 mol) is suspended in methylene chloride (200 ml) and acetyl chloride (44 g, 40 ml, 0.56 mol) is added to it. The reaction mixture is heated at 27°–30° C. for 4 hours with a clear colourless solution being thus obtained to which thionyl chloride (65.6 g, 40 ml, 0.56 mol) is added. The solution is kept heated at 38°–40° C. for 6–7 hours until the reaction is complete. The solution is concentrated to residue at 40° C./20 mbar with a pale yellow oil being thus obtained having a purity (by GLC, % area via methyl ester) of >98%, which is used as such in the reaction which follows.

EXAMPLE 13

[R-(R*,R*)]-2-(3-chlorophenyl)-N-[2-(3,4-dimethoxyphenyl)-1-methyl-ethyl]-2-acetoxy-acetamide

(20) [(R,R)-acetoxy-amide]

(R)-3,4-dimethoxyamphetamine (3) hydrocloride (100.0 g, 0.432 mol) is suspended in methylene chloride (500 ml);

a solution of 10% sodium bicarbonate (20 ml) is added until pH reaches a value of 6.5: the two-phase mixture is cooled down to 0° C. and simultaneously raw (R)-O-acetyl-3-chloromandeloyl chloride (19) (theoretical weight 105.7 g, theoretical molar content 0.429 mol) dissolved in methylene chloride (100 ml) and a solution of 15% sodium carbonate (200 ml), are dropwise added thereto during 1–2 hours, while keeping pH value always comprised within the range of from 6 to 7, at a temperature comprised within the range of from 0° C. to +5° C. When the addition is complete, the reaction mixture is brought to a stable pH value of 7.5 with 15% sodium carbonate, is heated up to 20° C. and is kept stirred at that temperature for several hours.

The organic phase is separated off and the aqueous phase is extracted with methylene chloride (100 ml). The combined organic phases are concentrated to residue at 35°–40° C./30 mbar, with a white solid being obtained.

Raw (R,R)-acetoxy-amide has a purity of 94–95% and contains from 3 to 4% by weight of (S,R)-diastereomer and from 0.5 to 1.0% by weight of residual (R)-3,4-dimethoxyamphetamine: it is used as such in the reaction which follows.

EXAMPLE 14

[R-(R*,R*)]-2-(3-chlorophenyl)-N-[2-(3,4-dimethoxyphenyl)-1-methyl-ethyl]-2-hydroxy-acetamide

(21) [(R,R)-hydroxyamide]

Raw (R,R)-acetoxyamide (20) (174 g, theoretical molar content 0.429 mol) is suspended in methanol (600 ml) and potassium hydroxide (6.0 g, 0.107 mol, 0.25 equivalents) is added to the suspension. The reaction mixture is kept stirred for 1 hour at 20°–22° C. until a clear solution is obtained: said solution is neutralized with acetic acid until a pH value of about 6 is obtained (6 ml) and the solution is cooled down to 0° C., temperature at which the product starts to crystallize: the crystallization is carried to completeness by adding water (600 ml) and keeping the resulting mixture at 0° C. for 2 hours.

The precipitate is filtered, the filter cake is washed with cold 50% aqueous methanol (150 ml) and is dried to constant weight (134–140 g, yield: 86–90%).

(R,R)-hydroxyamide (21) has the following characteristics:
Melting point: 123°–124° C.
$[\alpha]_D^{20}$ (C=2, MeOH) =−21.3° C.
Purity (by HPLC, % area)=97.6 % with 2.3 % by weight of (S,R)-hydroxyamide.
Mass spectrum=363 (M$^+$, 3%); 222 (5%); 178 (100%); 151 (35%); 77 (25%); 44 (50%)

EXAMPLE 15

[R-(R*,R*)]-1-(3-chlorophenyl)-2-[2-(3,4-dimethoxyphenyl)-2-methyl-ethyl-amino]ethanol (5)

[(R,R)-phenethanolamine CL 317,110]

(R,R)-hydroxyamide (21) (100.0 g, 0.274 mol) is dissolved in tetrahydrofuran (400 ml). The solution is refluxed under an inert atmosphere and then borane-dimethyl sulfide (70 ml~10M, approximately 0.70 mol, 2.55 equivalents) is dropwise added thereto in 1–1.5 hours. The reaction mass is kept under refluxing conditions for 1.5 hours, while approximately 70 ml being distilled off of a mixture constituted by dimethyl sulfide and THF. The reaction mass is cooled down to 5° C. and methanol (120 ml) is slowly dropwise added to it at a temperature comprised within the range of from 5° C. to 25° C.

The reaction mixture is kept stirred for 15 minutes at 20° C. and 20% (w/v) hydrochloric acid in methanol (60 ml) is dropwise added thereto. The solution is heated under refluxing conditions for 30 minutes in order to decompose the borane complex with phenethanolamine and then it is cooled down to 30° C. and is concentrated to residue at 35°–40° C./20 mbar, with a colourless oil being thus obtained, which is constituted by (R,R)-phenethanolamine hydrochloride (5).

The residue is taken up with methylene chloride (300 ml) and water (150 ml) and the mixture is brought up to a sharply alkaline pH value with 30% sodium hydroxide (40 ml): the organic phase is separated and the aqueous phase is extracted with methylene chloride (150 ml). The combined organic phases are washed with water (200 ml) and are concentrated to residue at 40° C./20 mbar: a nearly colourless oil is thus obtained which slowly crystallizes (about 95–96 g, yield: 100%).

| GLC analysis (silanized, % area) = (R,R) + (S,R)-phenethanolamine: 98.5% | |
|---|---|
| Mass spectrum: | 331(M-H$_2$O, 3%); 208(12%); 198 (30%); 180(95%); 151(100%); 139 (30%); 56(77%). |
| NMR spectrum (CDCl$_3$, TMS, 200 MHz) | 1.08(3H, d, J=70); 2.62(2H, d, J=6.5); 2.66(1H, d, J=8.7); 2.90 (2H, complex m); 3.87(6H, s); 4.53(1H, dd, J=8.7 and 3.7); 6.70(2H, d, J=11.2); 6.80(1H, d, J=7.8); 7.21–7.35(4H, complex m). |

EXAMPLE 16

[R-(R*,R*)]-(3-chlorophenyl)-3-[2-(3,4-dimethoxyphenyl)-1-methyl-ethyl]oxazolidin-2-one (1)

[(R,R-oxazolidinone CL 317,111]

Raw (R,R)-phenethanolamine (5) (theoretical weight 95.7 g, 0.274 mol) is dissolved in toluene (400 ml): butylene oxide (1,2-epoxybutane, 37.3 g, 0.518 mol, 1.9 equivalents) is added and then trichloro-methyl chloro-formate (36.1 g, 0.182 mol, 1.33 equivalents) is dropwise added to the resulting mixture during 60 minutes at a temperature comprised within the range of from 25° to 30° C. The reaction mixture is kept with stirring for 2 hours at 25° C. and concentrated ammonia (40 ml) and water (160 ml) are added. The reaction mixture is kept with stirring for several hours in order to secure the complete decomposition of the excess trichloro-methyl chloro-formate. The organic phase is separated, is washed with water (2×200 ml) and is concentrated to residue at 45° C./20 mbar.

The resulting pale yellow oil is dissolved in hot ethyl acetate (200 ml).

The solution is filtered through theorite and the filtrate is cooled down to 20° C.; hexane (400 ml) is slowly added to it.

The suspension is kept for 2 hours at 0° C: the product is filtered, is washed with a cold 4:1 mixture of hexane/ethyl acetate and is dried to constant weight (85–88.5 g; yield from hydroxyamide: 82.5–86%).

(R,R)-oxazolidinone (1) has the following analytical characteristics:

| | |
|---|---|
| Melting point: 80–81° C. | |
| $[\alpha]_D^{20}$ (C = 2, $CH_2Cl_2$) = −35.5° C. | |
| HPLC analysis: | 99.87% with 0.1% of (S,R)-diastereomer |
| GLC analysis: | >99.5% |
| Mass spectrum (m/e): | 375($M^+$, 4%); 224(6%); 180 (75%); 178(100%); 151(32%). |
| NMR spectrum ($CDCl_3$, TMS, 200 MHz): | 1.25(3H, d, J=6.8); 2.68(1H, dd, J=14.3 and 8.4); 2.80(1H, dd, J=14.3 and 6.4); 3.24(1H, dd, J=8.4 and 6.4); 3.8(1H, d, J=4.4); 3.8(3H, s); 3.85(3H, s); 4.35(1H, complex m); 5.35 (1H, dd, J=9.0 and 6.4); 6.6–6.7 (3H, complex m); 6.9(1H, d, J=7.4); 7.11–7.30(3H, complex m). |

We claim:

1. A process for the synthesis of [R-(R*,R*)]-5-(3-chlorophenyl)-3-[2-(3,4-dimethoxyphenyl)-1-methyl-ethyl]oxazolidin-2-One (1), which process is carried out according to Scheme IV and comprises the following reactions:

a) acetylation of (R)-3-chloromandelic acid (9) with the formation of (R)-O-acetyl-3-chloromandelic acid, which is then transformed into the corresponding acyl chloride, (R)-O-acetyl-3-chloromandeloyl chloride (19);

b) coupling of the chloride (19) with (R)-3,4-dimethoxy-amphetamine hydrochloride (3) to form the intermediate [R-(R*,R*)]-2-(3-chloro-phenyl)-N-[2-(3,4-dimethoxyphenyl)-1-methyl-ethyl]-2-acetoxy-acetamide (20) (illustrated as (R,R)-acetoxyamide in Scheme IV);

c) deacetylation of the intermediate (20) to form [R-(R*,R*)]-2-(3-chloro-phenyl)-N-[2-(3,4-dimethoxyphenyl)-1-methyl-ethyl]-2-hydroxy-acetamide (21) (illustrated as (R,R)-hydroxyacetamide in Scheme IV);

d) reduction of the amide group of the intermediate (21) to form the corresponding phenethanolamine, [R-(R*,R*)]-1-(3-chlorophenyl)-2-[2-(3,4-dimethoxy-phenyl)-1-methyl-ethylamino]ethanol (5); and e) formation of (R,R)-oxazolidinone (1) by reacting said phenethanolamine (5) (β-aminoalcohol) with a suitable reactant; and wherein Scheme IV is as follows:

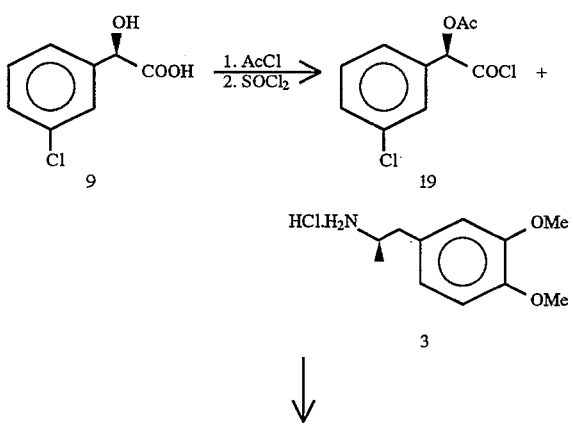

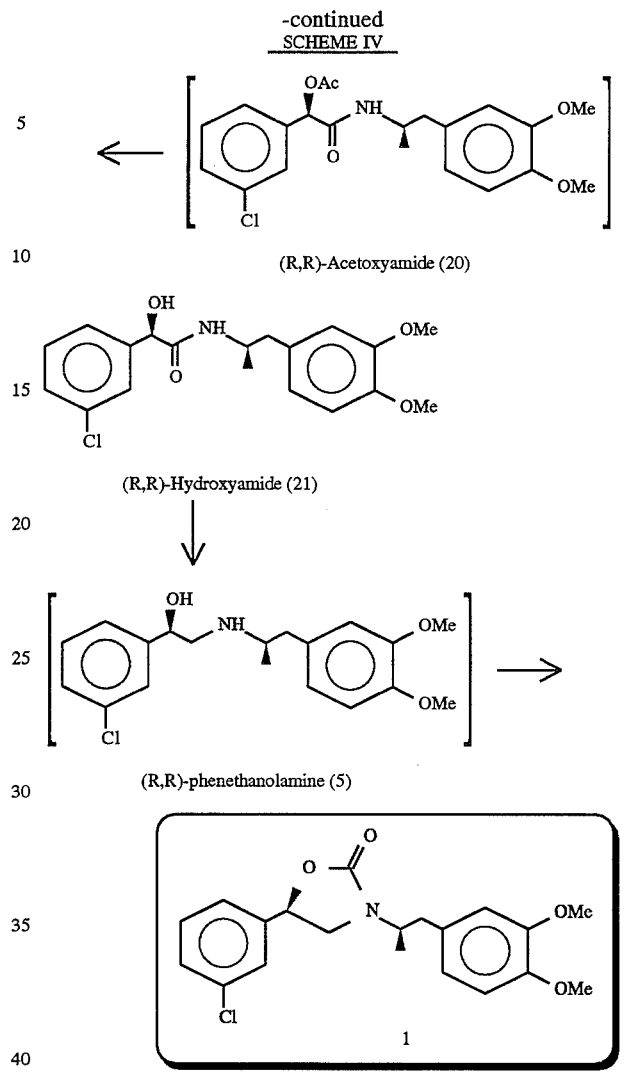

2. A process according to claim 1 wherein said (R)-3-chloromandelic acid of Formula 9 is formed by reacting a racemic mixture of 3-chloromandelic acid with (R)-α-methyl-benzyl-amine to form (R,R)-α-methyl-benzylammonium 3-chloro-mandelate salt, and then acidifying and extracting the latter by means of a suitable solvent.

3. A process according to Claim 1 wherein said (R)-α-methyl-benzyl-amine is used in a deficient stoiciometric mount based on said racemic mixture of (R)-3-chloromandelic acid, wherein a base is added, wherein said (R,R)-α-methyl-benzylammonium 3-chloro-mandelate salt is recrystallized frdm water, and is acidified and extracted by means of a solvent and, finally, is again crystallized, thus yielding the (R)-enantiomer of 3-chloromandelic acid of Formula (9) with a high purity level.

4. A process according to Claim 1, wherein said (R)-3,4-dimethoxy-amphetamine hydrodchloride of Formula (3) is prepared by condensing 3,4-dimethoxybenzaldehyde (10) with nitroethane (Henry's reaction) to form 3,4-dimethoxy-phenyl-2-nitro-propene (11), wherein said 3,4-dimethoxy-phenyl-2-nitro-propene is then reduced to 3,4-dimethoxy-phenyl-acetone (12) by means of a catalytic hydrogenation, wherein said 3,4-dimethoxy-phenyl-acetone (12) is then reacted with (R)-α-methyl-benzyl-amine (13) to form the corresponding chiral imine (14), wherein said chiral imine (14) is then diastereoselectively reduced to (R,R)-N-phenylethyl-3,4-dimethoxy-amphetamine (15) hydrochloride intermediate by means of a catalytic hydrogenation with Raney nickel with the intermediate (15) being then debenzylated by a further hydrogenation, thus yielding (R)-3,4-dimethoxy-amphetamine hydrochloride, according to the following reaction scheme:
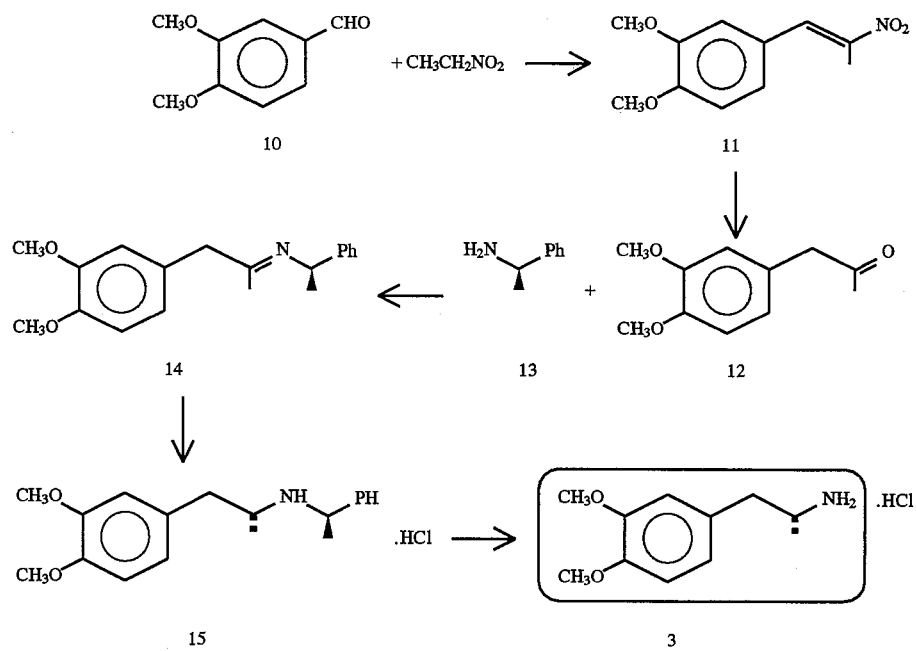
* * * * *